United States Patent [19]
Trerice et al.

[11] Patent Number: 5,173,662
[45] Date of Patent: Dec. 22, 1992

[54] METHOD AND ASSOCIATED APPARATUS FOR DETERMINING CARBON CONTENT IN FLY ASH

[76] Inventors: Douglas N. Trerice, 661 Surfside Dr., Pittsburgh, Pa. 15239; Charles R. Buffler, 126 Water St., Marlborough, N.H. 03455

[21] Appl. No.: 833,990

[22] Filed: Feb. 11, 1992

Related U.S. Application Data

[63] Continuation-in-part of Ser. No. 448,125, Dec. 8, 1989, Pat. No. 5,109,201.

[51] Int. Cl.⁵ ............................................. G01N 22/00
[52] U.S. Cl. .................................... 324/642; 324/639; 73/28.01
[58] Field of Search ............... 324/637, 639, 641, 642; 73/28.01, 28.04; 340/627; 110/216, 165 R, 165 A

[56] References Cited

U.S. PATENT DOCUMENTS

| | | | |
|---|---|---|---|
| 4,580,441 | 4/1986 | Sakurai et al. | 324/639 X |
| 4,663,507 | 5/1987 | Trerice | 219/10.55 M |
| 4,705,409 | 11/1987 | Trerice | 219/10.55 M X |
| 4,941,083 | 2/1990 | Ohno et al. | 324/637 |

FOREIGN PATENT DOCUMENTS 872094  7/1961  United Kingdom .

OTHER PUBLICATIONS

Trerice et al., A New Method For Improving the Salability of Fly Ash., Mar. 1988, pp. 1-16.

Primary Examiner—Jack B. Harvey
Attorney, Agent, or Firm—Floyd Scheier

[57] ABSTRACT

A method for determining carbon content in fly ash includes providing a source of fly ash and a microwave interrogation chamber. A quantity of fly ash is introduced into the interrogation chamber and exposed to microwave energy. The amount of carbon in the fly ash is determined by measuring the amount of microwave energy exposed to the fly ash, the amount of energy transmitted through the fly ash, and the amount reflected therefrom in order to determine the amount of energy absorbed. The concentration of fly ash is preferably determined by determining the weight of the fly ash and determining the percentage of carbon content in the fly ash. The method is particularly useful in respect of monitoring carbon content in fly ash of boiler exhaust gases. The system may also be employed to determine the fly ash glass content of fly ash. An associated apparatus is also disclosed.

23 Claims, 6 Drawing Sheets

METHOD AND ASSOCIATED APPARATUS FOR DETERMINING CARBON CONTENT IN FLY ASH

This Patent Application is a Continuation-In-Part Patent Application of Co-pending U.S. patent application Ser. No. 07/448,125 filed Dec. 8, 1989, now U.S. Pat. No. 5,109,201.

BACKGROUND OF THE INVENTION

1. Field of the Invention

The present invention provides a system for determination of the carbon concentration in fly ash and, more specifically, it permits automated determination of the amount of carbon in fly ash by interrogating the fly ash with microwave energy and determining the amount of microwave energy absorbed thereby.

2. Description of the Prior Art

The importance of determining the carbon content of fly ash, such as is produced in coal burning boilers, has long been known. For example, fly ash can be a marketable combustion product for utility companies which burn coal in order to generate electrical energy. In general, when carbon levels are greater than about 3 percent in fly ash, the fly ash becomes unsalable. Fly ash is known to be usable in the cement replacement market.

When the carbon content is too high to permit marketing of the fly ash to such users as the cement replacement market or the ready mixed concrete producers, not only is there a loss of potential sales revenue, but also there is the burden of disposal costs.

The quantity of fly ash carbon may also be viewed as a loss of potential fuel due to less than complete burning. Determination of unburned carbon by conventional methods is time consuming, and as a result, is not available to plant operators on a timely basis. If there were a way of determining carbon content promptly, adjustments could be made to the combustion process that would minimize carbon content in the fly ash, i.e., unburned fuel loss.

Among other known uses of fly ash are as fillers in plastics and asphalt, as a source of activated carbon for water and sludge treatment, as a source of magnetite for coal cleaning as well as for use in structural fills and backfill embankments, landfill covers, soil amendment and pavement base courses.

It has been known that the carbon content in fly ash can be determined by employing microwave energy which passes through a fly ash sample and measuring the unabsorbed microwave energy. In one embodiment, temperature differential in a waterwall is measured. An electronic device, sensitive to microwave power is also suggested in a general manner. See U.S. Pat. Nos. 4,663,507 and 4,705,409. See also, a paper entitled "A New Method For Improving the Salability of Fly Ash" by Trerice and DiGioia presented at the American Public Power Association Engineering and Operations Workshop in New Orleans, La. on Mar. 15-17, 1988 which shows collection and interrogation apparatus.

Despite the foregoing known systems, there remains a real and substantial need for improved means for measuring the carbon content of fly ash in an efficient and timely manner.

SUMMARY OF THE INVENTION

The method of the present invention involves providing a source of fly ash and subjecting a quantity of the fly ash to an interrogation chamber wherein it is exposed to microwave radiation. A quantity of fly ash is introduced into the interrogation chamber and exposed to the microwave energy for a predetermined period of time. The amount of carbon in the fly ash is determined by measuring the amount of microwave energy exposed to the fly ash, the amount of microwave energy passing through the fly ash and the amount of microwave energy reflected by the fly ash. These determinations may be employed to ascertain the amount of microwave radiation absorbed by the fly ash. These data permit a determination of the percentage of carbon in fly ash to be made.

Computers may be employed to compute the amount of microwave energy absorbed by the fly ash along with the amount transmitted and reflected and the percentage concentration of carbon can be determined. The quantity of fly ash delivered to the interrogation chamber may be measured.

The apparatus of the present system preferably has a collection system which will capture a gaseous stream having entrained fly ash, a means for separating the fly ash from the gaseous stream, and returning the gaseous stream to a main duct. The main duct may advantageously be the exhaust duct from a coal fired boiler. A quantity of fly ash is interrogated within the interrogation chamber by means of the microwave energy. Means are provided for determining (a) the amount of microwave energy being delivered to the interrogation chamber, (b) the amount of microwave energy passing through the fly ash, and (c) the amount of microwave energy reflected by the fly ash and converting this information into a determination of the quantity of carbon and the quantity of fly ash.

It is an object of the present invention to provide a method and associated apparatus for measuring the carbon content in fly ash in an efficient and rapid, automated manner.

It is a further object of the present invention to provide such a system wherein precise determination of the carbon content may be obtained through the use of microwave energy.

It is a further object of the present invention to provide such a system that determines the amount of the fly ash sample being analyzed.

It is another object of the present invention to provide a process wherein carbon content of fly ash may be determined through a sampling procedure which extracts fly ash laden exhaust gases at a velocity corresponding to the velocity of the same through the main exhaust duct.

It is a further object of the present invention to provide such a system which resists undesired escape of microwave radiation from the apparatus.

These and other objects of the invention will be more fully understood from the following description of the invention with reference to the illustrations appended hereto.

DESCRIPTION OF THE PREFERRED EMBODIMENTS

Figure 1:
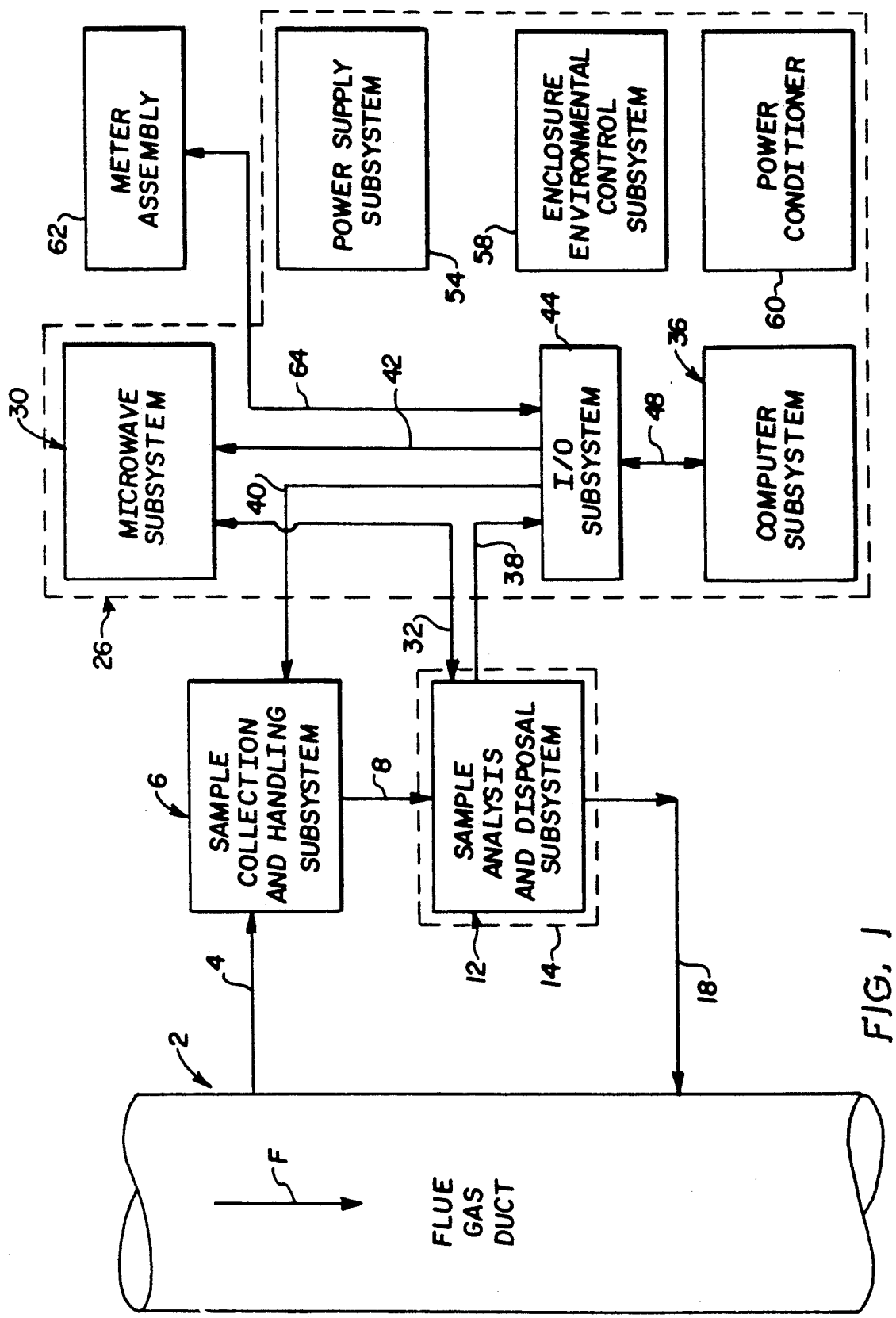
FIG. 1 is a system architecture diagram showing the system for employing microwave energy to determine the carbon concentration of fly ash.

The term "fly ash" as used herein refers to solid products of combustion, including, but not limited to coal combustion.

Referring once again to FIG. 1, there is shown a block diagram of an overview of the system of the present invention. There is shown a main duct 2 through which the boiler exhaust gases pass in the direction indicated by the arrow F. The exhaust gases pass through the main duct interior toward an electrostatic precipitator or other particulate collection device (not shown).

The flue gas to be analyzed will be withdrawn from the main duct by any suitable means known to those skilled in the art. The gas which is removed contains particles of fly ash entrained therein and will pass through duct 4 to sample collection and handling subsystem 6. This system 6 is responsible for collecting fly ash samples and releasing the sample to the interrogation cell. The interrogation cell is contained within the sample analysis and disposal subsystem 12 which preferably has a sealed surrounding protective enclosure 14. This subsystem 12 is sealed so that it is of the same pressure as duct 2. The exhaust gases from which the fly ash sample has been removed are then returned to the main duct 2 through duct 18 which in the form shown is downstream of duct 4.

It is preferred that the means for withdrawing fly ash containing exhaust gas from the main duct accomplishes withdrawal in such a manner that the sample will have a velocity and fly ash concentration generally equal to that of the main duct 2. Such systems are known to those skilled in the art.

The electronic processing system is shown within the dashed enclosure 26. The microwave subsystem 30 determines the carbon and fly ash weight of the fly ash samples introduced into the interrogation cell which is disposed within the sample analysis and disposal subsystem 12 with which it is in communication by electrical lead 32. The computer subsystem 36 is in communication with the sample analysis and disposal subsystem 14 by means of electrical lead 38. It is also in communication with the sample collection and handling subsystem 6 by means of electrical lead 40 and in communication with the microwave subsystem 30 by electrical lead 42. All of these connections are made through intermediate interface input/output subsystem 44 and electrical lead 48. The computer subsystem 36 is responsible for the integrated control of the other subsystems, as well as the calculation of the carbon content and the driving of the displays.

Figure 2:
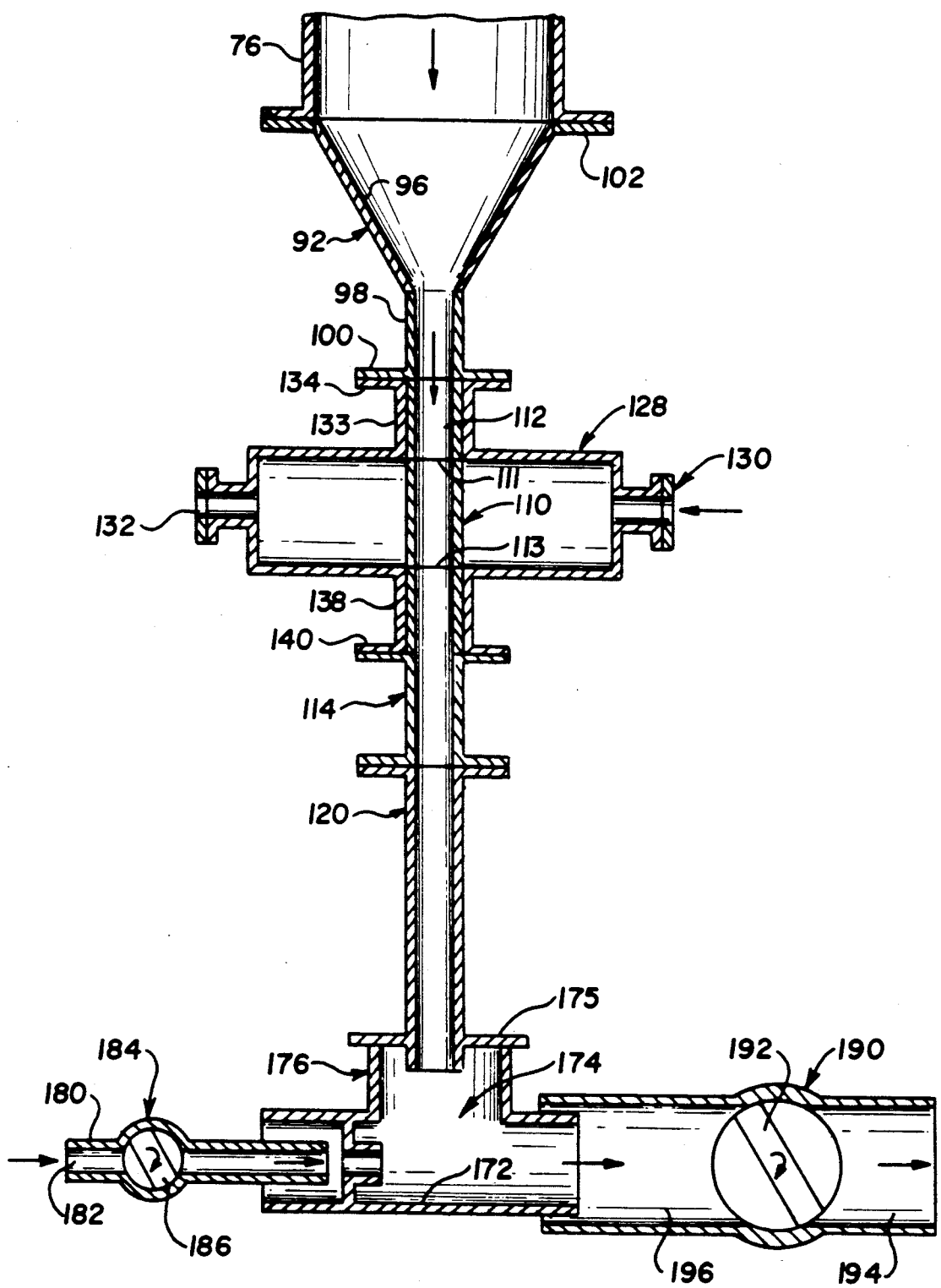
FIG. 2 is a partially schematic cross-sectional illustration showing an interrogation chamber of the present invention.

With reference to FIG. 2, a brief description of the system will be provided in order to enhance full comprehension of the system. The cycle of operation begins with the collection of a sample of fly ash in the delivery column 76 which is preferably the outlet portion of a cyclone separator. Delivery column 76 is in communication with and receives fly ash from the separator. Delivery column 76 is also in communication with underlying chamber 112 of the interrogation cell 110.

The fly ash collection system collection rate is determined by the concentration of fly ash in the duct F and the area of the sample probe. If it is desired to collect fly ash at an increased rate, the probe cross-section may be increased. For example, the system may be so configurated that the interrogation cell will receive 10 grams of fly ash and employ a three minute collection and interrogation time. If desired, increased speed could be employed to provide an update on carbon every minute.

Also shown within the dashed line enclosure 26 of FIG. 1 are the power supply subsystem 54 which is responsible for providing power at the correct voltage for use by other subsystems. It also preferably contains means for establishing an uninterrupted power by means of power conditioner 60 of appropriate quality to the system in the event of AC voltage fluctuations or dropouts.

The power supply subsystem 54 preferably includes an uninterruptable AC power supply and several DC power supplies which provide power to the various system components. This serves to continue desired operation even during power fluctuations and sags and preserves time-average reading data on the total loss of power. It is preferred that the battery and the power supply be sized for about one-half hour of operation.

The enclosure environmental control system 58 controls the temperature of the electronics enclosure 26 and the purge air into the enclosure 26. The enclosure environmental control subsystem 58 may consist of an externally mounted air conditioner for temperature control combined with a fan and filter system to introduce clean purge air into enclosure 26. It is desired to maintain a temperature of generally about 80° F. to 90° F. within the enclosure 26 in order to reduce temperature-induced drift in the instruments and to enhance reliability.

The computer subsystem 36 through the input/output subsystem 44 is in communication with the meter assembly 62 through lead 64. The meter assembly 62 provides a visual indication of the carbon concentration, carbon flow rate and fly ash flow rate in order to permit the control room operator to employ this information in the operation of the boiler. The operator can select either instantaneous or average readings, as desired.

The sample collection and handling system 6 gathers the fly ash, preferably using an isokinetic probe inserted into the main flue gas duct 2. A suitable form of probe and sample collection system for the purpose is that disclosed in British patent 872,094. Although other systems may be employed for this purpose, a cyclone separator may be employed to separate the fly ash from the flue gas from duct 4 and return the flue gas to the duct through duct 18. It is preferred that the fly ash collect in the bottom of the separator and move into the interrogation cell 110 under the influence of gravity. Suitable valves (not shown) well known to those skilled in the art may be employed to isolate the interrogation cell 110 from the negative pressure of the separator.

Referring once again to FIGS. 1 and 2, the fly ash removed from the gaseous stream in main duct 2 will drop under the influence of gravity into the delivery column 76 and be delivered by the entry column 92 to interrogation cell 110. The fly ash while in the interrogation cell 110 will be subjected to microwave radiation generated by microwave generator 130. Computer subsystem 36 also receives information regarding the amount of microwave power presented to the sample, the amount of microwave power passing through the fly ash sample and the amount of power reflected from the sample. On the basis of this information, it computes the amount of microwave energy absorbed by the fly ash. This absorption amount may be converted into the amount of carbon and the amount of fly ash. This permits determination of both the amount of carbon in the fly ash and the percentage of carbon in the fly ash. The fly ash flow rate and carbon content are determined in the computer subsystem 36 and are fed through input/output subsystem 44 over lead 64 to meter assembly 62 which provides a visual readout for the benefit of an operator or may be stored and, if desired, may be employed to automatically adjust the boiler to produce less carbon.

Referring to FIG. 2 in greater detail there is shown the delivery column 76 from which fly ash will pass under the influence of gravity. The fly ash is received in column 92 which in the form shown has a downwardly tapered tubular upper portion 96, a generally cylindrical lower portion 98 and generally radially outwardly projecting annular flanges 100, 102. Microwave chokes 111, 113 are positioned respectively in the upper and lower ends of the portion of interrogation tube 110 within which the fly ash sample being interrogated will be received. These chokes have an open mesh which will permit passage of fly ash particles of desired size therethrough. These chokes also resist undesired escape of microwaves from the effective interrogation volume which is the section of interrogation tube 110 between the chokes 111, 113. The size of mesh opening in choke 113 will preferably be of the same size as those of choke 111. The openings, for example, may be on the order of about ⅛ to 3/16 inch. The chokes 111, 113 are made of an electrically conductive material and are grounded to the microwave circuit.

The interrogation tube 110, which is preferably of circular cross-sectional shape, is composed of a material which permits the passage of microwaves therethrough, but not the passage of fly ash therethrough. Among the suitable materials for this purpose are glass, alumina, quartz, and materials available under the trade designations Teflon and Pryex. Fly ash will descend preferably under the influence of gravity through the interior 112 of interrogation tube 110 into the effective interrogation volume defined by chokes 111, 113. This provides for a predetermined volume of fly ash to be tested.

Disposed in adjacent relationship with respect to interrogation tube 110 is an elongated waveguide 128 which has a longitudinal axis oriented generally perpendicularly with respect to the axis of the interrogation tube 110. The wave guide 128 may have a generally rectangular cross-sectional configuration. Microwave energy entering input 130 will pass through interrogation tube 110 and to the extent not absorbed by the fly ash disposed within the effective interrogation volume o reflected by the fly ash will be received at the output end 132. The waveguide 128, in the form shown, has an upwardly projecting tubular portion 133 which terminates in an annular flange 134 which is secured in intimate surface-to-surface contact with flange 100. Portion 133 is in surface-to-surface contact with the outer surface of interrogation tube 110. Similarly, downwardly projecting tubular portion 138 terminates in an annular flange 140 and is in surrounding surface-to-surface engagement with interrogation tube 110.

Eductor 174 is hollow and defined by annular member 176 which is in intimate contact with annular flange 175 of tubular section 120 and the underlying annular portion 172.

During testing, the fly ash may be in the form of a column resting on element 172 of eductor and exiting up to choke 111 or may be supported on a closed valve (not shown) disposed within interrogation tube 110 underlying choke 113.

In order to withdraw the fly ash from the column 110 after interrogation has been accomplished, it is preferred to employ automated means. A source of pressurized air is in communication with tube 180 which defines passageway 182. When the eductor valve 184 is opened such that its passageway 186 is opened to and in communication with passageway 182, pressurized air enters the eductor and urges the fly ash in the direction indicated by the arrows. When the charge of fly ash disposed on element 172 of eductor 176 is to be discharged, the discharge valve 190 is also opened so that passageway 196 is opened with passageway 194 of discharge tube 196. Coordinated operation of the two valves 184, 190 will readily effect both opening and closing of the two valves in coordinated fashion.

The samples emerging from passageway 194 may be returned automatically to the main duct 2 employing the pressurized air and a partial vacuum on the downstream side created by the duct 2. If desired, further valving may be provided to facilitate withdrawal of a sample from the system for examination.

It will be appreciated that the movement of fly ash in a downwardly direction preferably under the influence of gravity will cause the fly ash sample to be exposed to microwave radiation. In a manner hereinbefore described and to be described in greater detail hereinafter, the amount of the power delivered (PF) to the fly ash which is absorbed by the fly ash is determined by measuring the amount of microwave radiation reflected off (PR) of the fly ash and passing through the fly ash (PT). The amount of microwave power absorbed permits a determination of the amount of carbon in the fly ash, the amount of fly ash, and the carbon concentration.

The microwave is preferably at a frequency of about 2,450 MHz. This may be supplied by the microwave generator by any conventional means.

In operation of the system as shown in FIG. 2, fly ash is continually fed to interrogation chamber 110 at the rate it is collected by the sample collection and handling system. The computer subsystem 36 continuously monitors the microwave power reflected and the microwave power transmitted. When fly ash in interrogation cell 110 reaches the bottom of waveguide 128, i.e., the level of choke 113, the computer subsystem 36 picks up a change in the reflected power and power transmitted and records a start time. The reflected power and transmitted power continues to vary until the level of the fly ash in interrogation cell 110 reaches the top of waveguide 128, i.e., the level of choke 111. At that time computer subsystem 36 records a stop time and records the reflected power and transmitted power. These final readings may be employed to calculate the carbon weight, carbon concentration and fly ash glass weight. The elapsed time between the start time and stop time may be employed to calculate sample system (collection rate). As the sample collection rate is proportional to the flow rate in duct F, a duct flow rate for carbon and fly ash may be calculated by the computer subsystem 36. The computer subsystem then initiates a purge cycle to remove the fly ash sample from interrogation cell 110.

Assuming for purposes of example, as is generally the case that the fly ash has two primary components, i.e., fly ash glass and carbon that respond to microwave these components, will each reflect and absorb microwave power. For such a sample, the power transmitted (PT) may be determined in accordance with Equation 1.

EQUATION 1

$$PT = (FAGwt \times a1) + (Cwt \times b1) + K1$$

The power reflected may be determined by Equation 2.

EQUATION 2

$$PR = (FAGwt \times a2) + (Cwt \; c \; b2) + K2$$

Wherein:
PT = Power Transmitted Through the Sample
PR = Power Reflected by the Sample
FAGwt = Fly Ash Glass Weight
Cwt = Carbon Weight
a1, a2, b1 and b2 = Absorbability Coefficients
K1 and K2 = Interrogation Chamber and Equipment Losses Tests were performed on samples having different carbon contents to determine values for these coefficients and constants. These tests produced the following values:

| | |
|---|---|
| a1 = 0.027 | b2 = 0.159 |
| a2 = 0.012 | k1 = 0.277 |
| b1 = 0.047 | k2 = 0.444 |

By solving Equations 1 and 2, the values of FAGwt and Cwt for a particular PF level and interrogation chamber geometry may be determined.

Carbon concentration may be determined by Equation 3.

EQUATION 3

Carbon Concentration (%) = Cwt/Cwt & FAGwt

The duct carbon flow rate may be calculated by Equations 4 through 6.

EQUATION 4

Duct Carbon Rate = CCD × vD × AD

EQUATION 5

Sampler Carbon Rate = CCS × vS × AS

Wherein
CCD = Carbon Concentration in Duct
VD = Duct Velocity F
AD = Duct Area
CCS = Carbon Concentration in Samples Probe
VS = Sampler Probe Velocity
AS = Sampler Probe Area As CCD equals CCS and vD equals vS, then Duct Carbon Rate = (Sample Carbon Rate × AD)/AS In a similar manner, the system of the present invention may be employed to calculate the duct fly ash flow rate.

Figure 3:
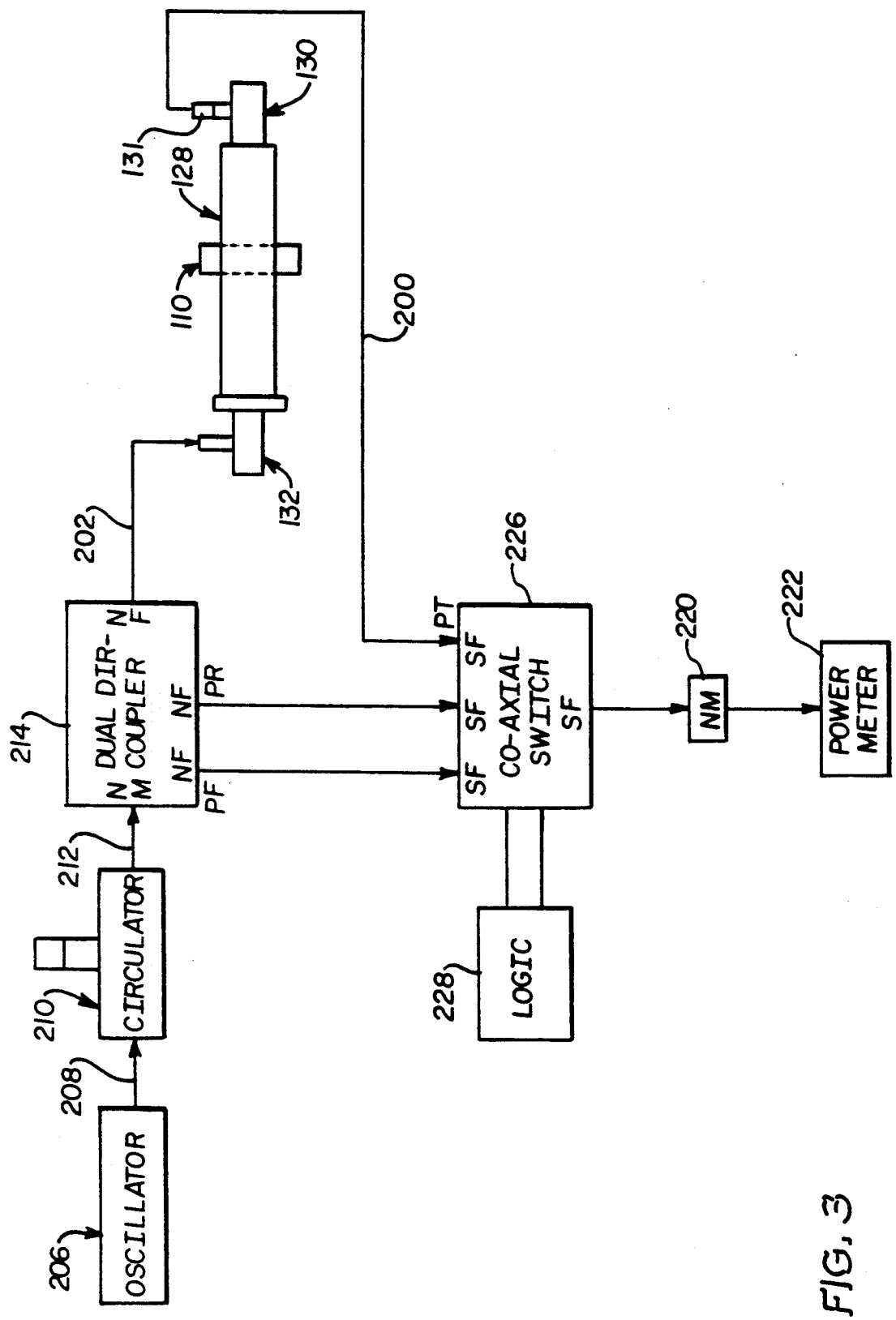
FIG. 3 is a block diagram of the microwave subsystem.

Referring in greater detail to FIG. 3, the microwave subsystem 30 will be described. As is shown in the upper right-hand portion of FIG. 3, the waveguide 128 has a first electrical lead 200 secured to the input 130 through attenuator 131 and a second electrical lead 202 secured to the output 132.

In the operation of this subsystem, the oscillator 206 generates microwave energy preferably at about 2,450 MHz frequency which is conducted by lead 208 to circulator 210 which allows the forward power to pass toward the waveguide 128 and by lead 212 to dual directional coupler 214 which is connected with waveguide outlet 132 by cable 202. The dual directional coupler 214 distinguishes between forward power and reflected power. The input sensor 220 of the power meter 222 is connected by coaxial switch assembly 226 to the transmitted power pickoff PT, the reflected power pickoff PR, and the forward power pickoff PF. Logic unit 228 which is part of computer subsystem 36 (FIG. 1) serves to control operation of the switch 226 to provide the desired mode. The computer subsystem 36 operates coaxial switch 226 to determine microwave power forward, reflected power, and power transmitted through the sample.

The carbon percentage of the sample is equal to the carbon weight divided by the sample weight and multiplied by 100 percent. The sample weight in turn is equal to the carbon weight plus the fly ash glass weight.

The sample analyzer and disposal subsystem 12 contains the interrogation cell 110.

The input/output subsystem 44 and the computer subsystem 36 preferably contain a microprocessor which may be programmed in any language in a manner well known to those skilled in the art. It will preferably be retained in EPROM or battery-packed RAM. The input/output subsystem 44 serves to provide interfaces with the computer subsystem 36 and the other various subsystems. A brief description of the system will be provided in order to enhance full comprehension of the system. The cycle of operation begins with the collection of a sample of fly ash in the holdup column 76 which is in communication with and receives fly ash from the separator and the chamber 112, 116 of the interrogation cell 110.

The quantity of sample introduced into the holdup column 76 is continuously fed from holdup column 76. The air control valve for the sample metering valves is preferably a 24 VDC solenoid operated valve.

Figure 4:
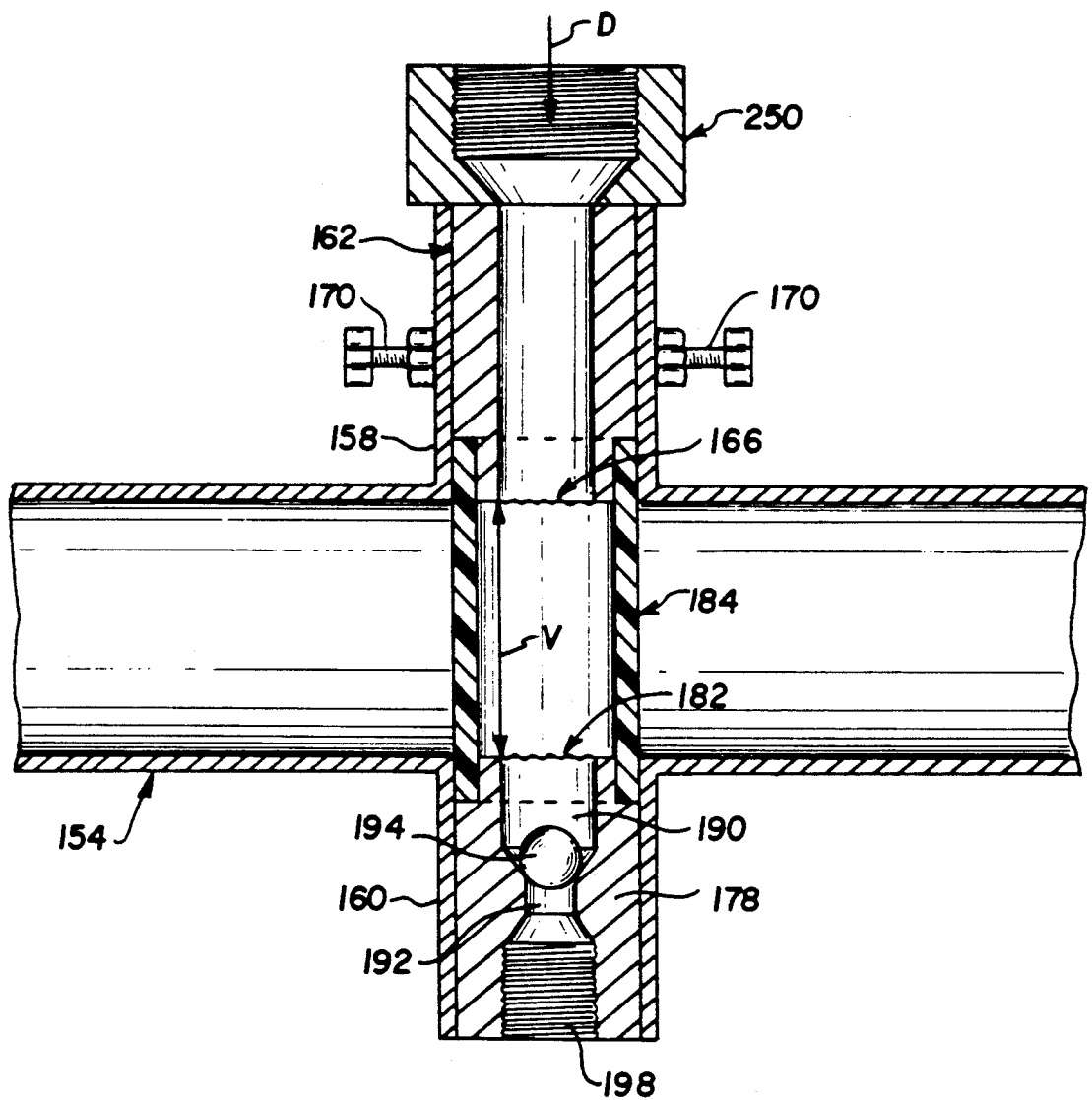
FIG. 4 is a schematic cross-sectional illustration of a modified system of the present invention.

Referring to FIG. 4, there is shown a modified system for removing fly ash from the interrogation chamber after it has been tested. Fly ash enters the system through delivery tube 250 in the direction indicated by arrow D. Microwave guide 154 has upwardly and downwardly directed extensions 158, 160. A tubular insert 162 is disposed within extension 162 and is in intimate contact therewith. Insert 162 is preferably composed of brass or another electrically conductive material. At the lower extremity of insert 162 is choke 166. Electrical contacts 170, 172 are respectively secured to the insert 162 and upper extension 158. Similarly, insert 178 is disposed interiorly of lower extension 160 and supports choke 182. Interrogation tube 184 has its ends received within recesses of inserts 158, 160. The effective interrogation volume V is the distance between opposed interior walls of waveguide 154 which is generally equal to the distance between the chokes 166, 182.

Insert 178 also serves as a valve. An upwardly open recess 190 is in communication with a lower passageway 192. A ball valve element 194 is normally seated in recess 190 by gravity to close passageway 192 and block communication with recess 190. When ball element 194 is in the seated position as shown in FIG. 4, the fly ash will have its column supported on the valve. When the test has been completed, in this embodiment, the fly ash is withdrawn by introducing compressed air through opening 198 to unseat valve element 194 and blowing the fly ash out through delivery tube 250. The next cycle of testing may then be initiated. This embodiment eliminates the need for eductor 174 of the other embodiment.

If desired, a vibrator may be employed to consolidate the fly ash sample within the effective interrogation volume.

Referring once again to FIG. 1, there is shown a block diagram of an overview of the system of the present invention. There is shown a main duct 2 through which the boiler exhaust gases pass in the direction indicated by arrow F. The exhaust gases pass through the main duct interior toward an electrostatic precipitator or other particulate collection device.

The flue gas to be analyzed will be withdrawn from the main duct by any suitable means known to those skilled in the art. The gas which is removed contains particles of fly ash entrained therein and will pass through duct 4 to a sample collection and handling subsystem 6. This system 6 is responsible for collecting fly ash samples and releasing the collected sample to the sample analysis and disposal subsystem 12.

It is preferred that the means for withdrawing exhaust gas containing fly ash from the main duct is accomplished in such a manner that the velocity and concentration within the sampler will be the same velocity and concentration as in the duct at the point of sampling. Such systems are known to those skilled in the art. More than one sample withdrawal point may be utilized to remove flue gas and entrained particulate from duct 2. Because duct flow as indicated by arrow F and particulate concentration varies from one position in duct 2 to another position in duct 2, the amount of entrained material collected by the an individual withdrawal system will vary from that collected by another withdrawal system.

A means is provided in the present invention to weigh collected sample from each individual withdrawal system and measure the time of collection for each individual withdrawal system so that the collection rate for each sampling point can be ascertained. The individual withdrawal system collection rates, particulate concentrations and carbon concentrations are then combined by computer assisted means to produce a composite collection rate and composite carbon concentration for the combined individual withdrawal systems, that more closely approximate the actual duct conditions.

The interrogation cell is contained within the sample analysis and disposal subsystem 12 which preferably has a sealed surrounding protective enclosure 14. This subsystem is sealed so that it is of the same pressure as duct 2. The exhaust gases from which the fly ash sample has been removed are then returned to the main duct 2 through duct 18 which in the form shown is downstream of duct 4.

The electronic processing system is shown within the dashed enclosure 26. The microwave subsystem 30 determines the sample weight, consisting of principally fly ash glass and carbon, and the microwave properties, that is, the reflected power and the transmitted power of the sample that is collected by the sample analysis and disposal subsystem 12. Electrical means of communication are provided between microwave subsystem 30 and sample collection and disposal subsystem 12 by electrical lead 32. The computer subsystem 36 is in communication with the sample analysis and disposal subsystem 14 by means of electrical lead 38. It is also in communication with the sample collection and handling subsystem 6 by means of electrical lead 40 and in communication with the microwave subsystem 30 by electrical lead 42. All of these connections are made through intermediate interface input/output subsystem 44 and electrical lead 48. The computer subsystem 36 is responsible for the integrated control of the other subsystems, the calculation of the carbon content, the measurement of the weight of collected sample and the driving of the displays.

In the present embodiment, more than one sample collection and handling subsystem 6 may be provided. An equivalent number of sample analysis and disposal subsystem 12 may be provided to match each sample collection and handling subsystem 6 so that simultaneous sampling and interrogation from individual sample withdrawal systems can be provided. The computer subsystem 36 will then measure the sample collection rate from each sample collection and handling subsystem 6 and combine the individual subsystem measurement results to ascertain a combined effect.

In one embodiment of the present invention, more than one sample collection and handling subsystem 6 would be provided with only one sample analysis and disposal subsystem 12. By proper valving to isolate individual sample collection and handling subsystem 6, as known to those versed in the art, individual samples from each sample collection and handling subsystem 6 can be processed individually and sequentially by one sample analysis and disposal subsystem 12.

Figures 5, 6, 7, 8:
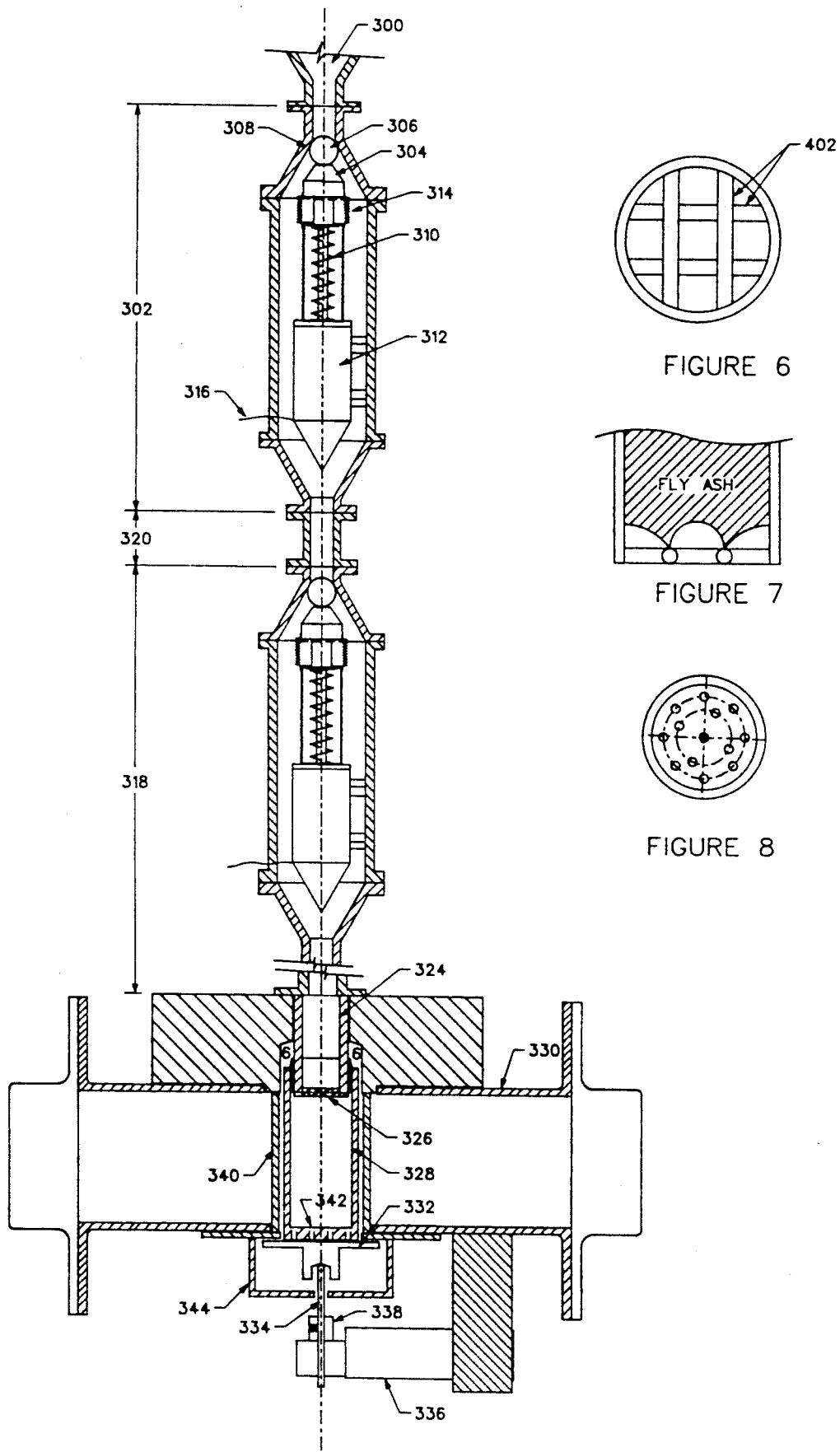
FIG. 5 is a partial schematic cross-sectional illustration of another embodiment of the present invention.
FIG. 6 is a partial schematic illustration of a filling tube choke taken along Line 6—6 of FIG. 5.
FIG. 7 is a partial schematic illustration of the choke wire relationship.
FIG. 8 is a partial schematic illustration of the interrogation cell bottom.

With reference to FIG. 5, a brief description will be provided of the sample analysis and disposal subsystem 12 that provides a composite measurement of carbon concentration in fly ash when more than one sample collection and handling subsystem 6 is employed.

The cycle of operation begins with the system at rest and in the sample analysis mode. Particulate that has been collected and separated from exhaust gases in sample collection and handling subsystem 6 is introduced to the sample analysis and disposal subsystem 12 through a conduit 300, preferably the outlet portion of a cyclone separator or filter. The solid material drops by gravity to a specifically designed valve assembly 302 that consists of a plunger 304, plunger tip 306, seat 308, spring 310 and electric coil 312 that works on the plunger 304. A flexible boot 314 made of rubber o of other suitable material is provided between and around the plunge 304 and electric coil 312 to prevent material from entering the electric coil 312. In the rest position the plunger 304 is held against the seat 308 by the pressure exerted by the spring 310. The spring 310 is designed to overcome the weight of the plunger and any pressure that is exerted on the plunger by the sampling collection and handling subsystem 6. The spring is of a helical nature, made of suitable stainless steel, and is available from various manufacturers. A typical manufacturer is Lee Spring Co. The plunger 304 and integral electric coil 312, commonly referred to as a solenoid, are available from suitable manufacturers such as Lucas Ledex, Inc. A series 20 model is used in the present embodiment but other models could be selected by those versed in the art depending on service factor and geometric dimensions. Electric leads 316 issue from the solenoid, through the valve assembly 302 enclosure and are connected to input/output subsystem 44 and communicate with computer subsystem 36 as described previously hereto.

Attached to the end of the plunger 304 is a spherical tip 306 that makes contact with a truncated cone of suitable top and bottom diameters, that forms the seat 308. Both the spherical tip 306 and seat 308 are machined from aluminum, but other materials such as stainless steel and brass could be used. The plunger tip 306 could be machined as a cone with identical dimensions as seat 308. In the rest position the plunger tip 306 and seat 308 are in intimate contact and this prevents the collected sample in conduit 300 from entering the remainder of the sample analysis and disposal subsystem 12. Also, the closed valve assembly prevents gas from flowing between the sample collection and handling subsystem 6 and the rest of the sample analysis and disposal subsystem 12. Also, the closed valve isolates the remainder of the sample analysis and disposal subsystem 12 from pressure fluctuations that are present in duct 2. When computer subsystem 36 issues a signal for the valve assembly 302 to open an electrical current passes through electrical leads 316 and energizes electrical coil 312 which causes a magnetic field to form and operate on plunger 304, pulling the plunger 304 into the electrical coil 312. The plunger tip 306, thus retracts from seat 308, allowing collected material to pass to a suitable conduit 320.

An identical valve assembly 318 is located below valve assembly 302 and is connected to valve assembly 302 with a suitable air tight conduit 320. When valve assembly 302 is opened, previously collected material as collected by the sample collection and handling subsystem 6 will pass through conduit 320 and be retained by valve assembly 318, that is normally in the closed position when valve assembly 302 is open. Before opening valve assembly 318, the computer subsystem 36 will interrupt electric current to electrical coil 312 allowing spring 310 to close plunger tip 306 against seat 308. Once valve assembly 302 is closed, computer subsystem 36 will direct valve assembly 318 to open and allow material to pass to the remainder of the sample analysis and disposal subsystem 12.

During the sample analysis cycle, the two valve assemblies are cycled in such a manner that one valve is always closed while the other is open to prevent transmission of gases between the sample collection and handling subsystem 6 and the remainder of the sample analysis and disposal subsystem 12 while allowing intermittent passage of collected material between the two subsystems 6 and 12.

Material passed by valve assembly 318 passes through fill tube 324, containing choke 326, and is collected by interrogation cell 328, that is enclosed in waveguide 330. Waveguide 330 is of normal manufacture and can be provided by Continental Microwave and Tool Co., Inc. The interrogation cell 328 bottom is supported by a flat surface platen 332, that is supported by pin support 334, that is in turn supported by load cell 336. Load cell 336 is of normal manufacture and can be supplied by Sensotech, Inc. A model MBL is provided herewith but various models of suitable construction and accuracy could be used by those versed in the art. The fill tube 324 is inserted within the top of interrogation cell 328 and acts as both a conduit for material discharged by valve assembly 318 and as a guide for the interrogation cell 328. The fill tube 324 restricts movement of the interrogation cell 328 in a lateral direction but allows the cell to move in a vertical direction. Loose clearances are provided between interrogation cell 328 and the exterior of fill tube 324 and between surface platen 332 and pin support 334 to minimize friction effects that will effect weight measurements. An adjustable collar 338 is around pin support 334 to allow vertical alignment of the flat surface plate 332 and thus allow vertical alignment of the interrogation cell 328 inside bottom to match the bottom inside of waveguide 330. A cylindrical shroud 340, made of glass, quartz, teflon or other microwave translucent material encloses interrogation cell 328, being directly connected between the top and bottom of waveguide 330. This shroud prevents material that may overflow the interrogation cell from accumulating within the waveguide 330.

Before material is allowed to pass through valve assembly 318, the computer subsystem 36 records the empty combined weight of the interrogation cell 328, platen 332, pin support 334 and pin support collar 338 by reading measurements made by load cell 336 and records the reflected power and transmitted power levels for the empty interrogation cell 328 by reading measurements taken by microwave subsystem 30. Each time that the valve assemblies 302, 308, are cycled, increments of material collect in the interrogation cell 328. The computer subsystem 36 records forward power, reflected power and transmitted power as measured by microwave subsystem 30, weight as measured by load cell 336 and the time of collection for each increment of material that is passed during each valve cycle. The incremental change in reflected power, transmitted power, weight, and time is calculated and stored by computer subsystem 36 for each succeeding addition of material to interrogation cell 328.

When collected material accumulates above choke 326, the incremental change in reflected power, transmitted power and weight approaches zero. FIG. 6 illustrates an end view of the choke 326. The choke 326, may comprise crossed, brass wires 402 or other suitable member that conduct electricity. The wires 402 are located within the end of the fill tube 324. The distance between the crossed wires 402 are in the range of ⅛ - 3/16 inch allowing material passage but restricting microwave passage. The wires 402 are brazed at their intersections and to the tube to provide good electrical contact. The choke wires 402 are aligned with the top inside surface of the waveguide 330.

The choke 326 prevents microwave from entering collected material that may be above the choke. The choke 326 is also specifically designed to allow collected material above the choke 326 to form a self-sustaining arch. The distance between wires 402 and the wire diameter are specifically chosen to create arching within the collected material.

FIG. 7 illustrates that arching begins to occur when material is allowed to fill above the choke wires 402. When the distance between the choke wires 402 are sufficiently small, the particles of collected material will transmit some of their weight to the choke wires 402 and to the fill tube 324 inside surface. Adjacent particles will also transmit a component of their weight to each other. Eventually this interlocking structure of particles, wires 402 and fill tube 324 surface prevents the weight of material above each self-sustaining arch to be transmitted to material below each arch, to the other collected material below the choke 326 and to the load cell 336. This self-arching action stops any further densification of collected material below choke 326 in interrogation cell 328. Incremental changes in reflected power and transmitted power that would be caused by densification are therefore avoided.

By comparing the time at which the interrogation cell 328 was empty to the time at which changes in incremental reflected power, transmitted power and weight approach zero, the computer subsystem 36 calculates the time that was taken to fill the interrogation cell 328. The collection rate is determined from the difference in weight from empty to full interrogation cell 328 divided by the time taken to collect the sample. The change in reflected power and transmitted power from empty to full interrogation cell is used to determine the carbon concentration of the collected material, as explained hereto.

When more than one sample collection and handling subsystem 6 is used to collect samples a composite carbon concentration can be determined using the following methods.

For each sample collection and handling subsystem 6 the collection rate is as follows:

$$WtRate = (WtFull - WtEmpty)/(TimeFull - TimeEmpty)$$

where:
  WtFull is the weight of the full interrogation cell 328, platen 332, pin support 334, collar 338, and collected material.
  WtEmpty is the weight of the empty interrogation cell 328, platen 332, pin support 334, and collar 338.
  TimeFull is the time at which the interrogation cell 328 is full as determined by little or no change in reflected power, transmitted power and weight.
  TimeEmpty is the time at the beginning of the valving cycle when the interrogation cell is empty.

The carbon collection rate for each sample collection and handling subsystem 6 can be determined as follows:

$$CarbonRate = \% Carbon * WtRate$$

Where:
  % Carbon is the calculated carbon concentration as determined by microwave subsystem 30 and computer subsystem 36 for each full interrogation cell 328 collected sample.
  WtRate is described above.

When, as an example, three sample collection and handling subsystems 6 are used to collect fly ash samples, the composite or weighted sample collection rate, that is, WeightedWtRate, for the three subsystems can be found using the following method:

$$WeightedWtRate = (WtRate1*Time1) + (WtRate2*Time2) + (WtRate3*Time3) \text{ all divided by} (Time1 + Time2 + Time3)$$

Where:
  The subscripts are associated with each separate sample collection and handling subsystem 6 collected samples and Time is the time that passed between empty and full interrogation cell 328 for each sample collected.

Similarly, the weighted carbon rate can be found by weighting individual collection and handling subsystem 6 CarbonRate with the time taken to collect a sample. A composite carbon concentration can be determined by dividing the weighted carbon rate by the weighted sample collection rate.

The interrogation cell 328 is fabricated of glass, quartz, teflon or of other suitable material that has low microwave reflection and absorptive properties.

The cell 328 includes a perforated bottom 342, as shown in FIG. 8, that facilitates emptying of the interrogation cell once interrogation and weighing have been completed. The perforated bottom 342 consists of a series of concentric holes of a diameter and number that both allow and restrict passage of air during the emptying sequence. The location of the holes must also provide complete emptying of the cell. Sufficient backflushing air must be passed by the holes to create a fluidizing action and to entrain collected material so that the interrogation cell can be fully emptied. Generally, depending on material properties a velocity of 30-50 feet per second is required to fluidize and entrain collected material. The size and number of holes are also chosen to restrict air flow and create a pressure drop that is sufficient to lift the interrogation cell and its contents. Generally, depending on the weight of the cell and its contents a pressure drop of 4-6 inches water column is sufficient to lift the assembly.

Again, referring to FIG. 5 the bottom of the cell is supported by a flat surface platen 332. The platen 332 and pin support connector 334 juncture provides a movable, self-adjusting surface for the bottom of the interrogation cell. The flat surface of the platen will adjust to any tilt in the cell to provide means that will not allow collected material in the interrogation cell 328 to leak out the cell bottom 342 through the cell bottom holes 342. The complete assembly is enclosed at the bottom of the waveguide 330 with another choke means 344 so that microwave cannot discharge from the assembly. A small hole is included in choke means 344 to allow pin support 334 to connect with load cell 336, to limit microwave leakage and to allow the passage of backflush air to empty the interrogation cell 328 as described hereto.

After the interrogation cell 328 is filled as determined by microwave subsystem 30 and computer subsystem 36, the emptying sequence is initiated by computer subsystem 36. Both valve assemblies 302 and 318 ar opened by energizing their electric coils.

Figure 9:
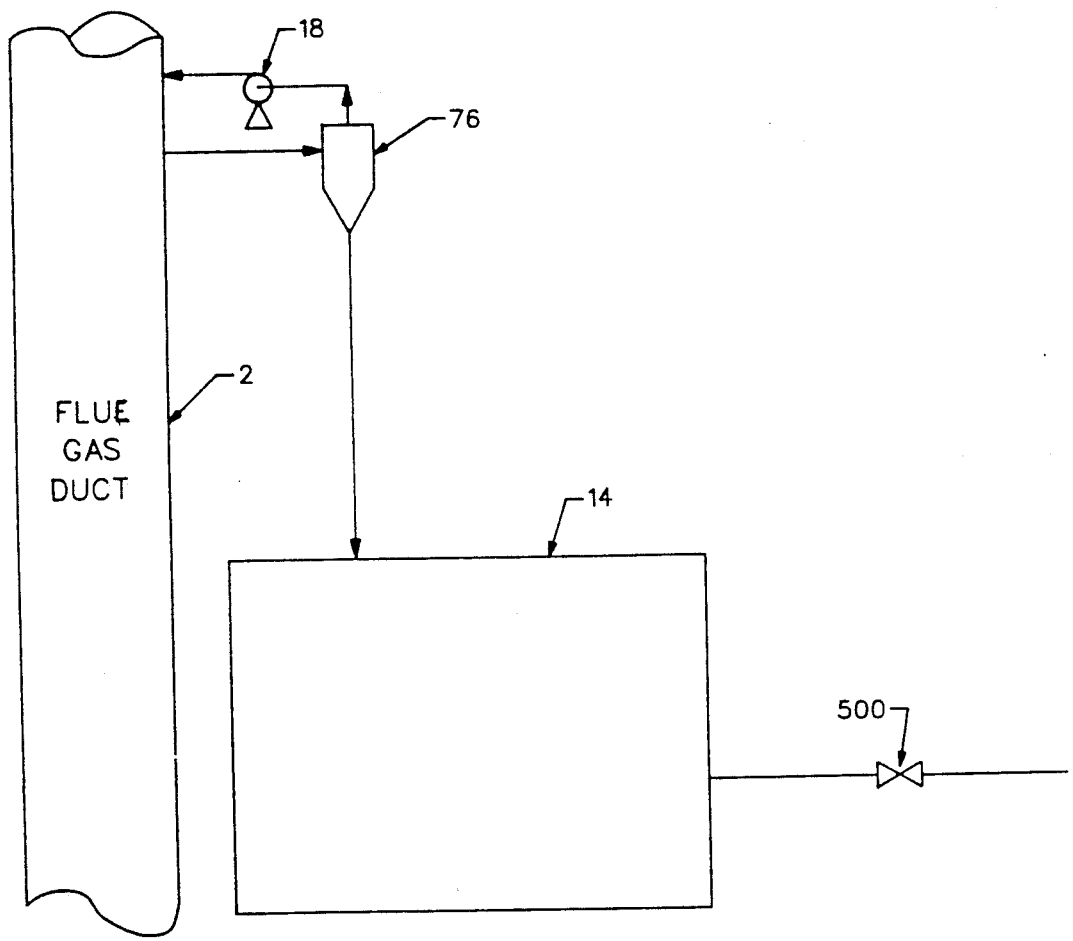
FIG. 9 is a partial schematic illustration of a interrogation cell purging method.

FIG. 9 illustrates valving that is required to conduct the emptying sequence in the present embodiment. Sample analysis and disposal subsystem enclosure 14 will have a pressure that is equivalent to duct 2 when interrogation cell 328 has filled. A means is provided wherein valve 500 can be opened once computer subsystem 36 determines that the interrogation cell 328 is full. Compressed air at elevated pressure above duct 2 pressure is provided to sample analysis and disposal subsystem enclosure 14 when valve 500 is opened. This pressure and flow is sufficient to lift both the interrogation cell 328 and the platen 332. The extent of lifting by the platen 332 is restricted by the bottom of the waveguide 330 and the cell 328 is allowed to rise further than the platen 332. This action exposes the interrogation cell 328 bottom perforations to gas flow. Gas flows through the perforations 342 and fluidizes the collected material and entrains the material back to duct 2.

Compressed air does not have to be supplied if sample analysis and disposal subsystem enclosure 14 is at sufficient negative pressure as compared to ambient to create enough flow through interrogation cell 328 to empty said cell of its contents, when valve 500 is opened to ambient.

After material has been discharged and the interrogation cell 328 is empty both valve assemblies 302 and 318 will close and valve 500 will close. The interruption of backflush gas flow allows the suspended interrogation cell 328 to settle on platen 332, and both settle on pin support connector 334, all of which settle on load cell 336.

It will be appreciated therefore that the apparatus and method of the present invention provides a means of extracting fly ash samples from various sample points, interrogating the individually collected samples for carbon content, and returning the collected samples to the point of capture. It will also be appreciated that a means has been provided to integrate more than one sample collection and handling subsystem 6 with one sample analysis and disposal subsystem 12 to obtain a more representative analysis of conditions in combustion duct 2. Valve assemblies 302 and 318 are shown to both isolate the sample analysis and disposal subsystem 12 from deleterious conditions transmitted by duct 2 and provide for the delivery of sample. A microwave based interrogation system is also shown to calculate carbon concentration for collected samples. Also, a means is provided to empty the interrogation system of interrogated sample so that a new sample can be taken and measured for carbon concentration. Finally a rapid method is developed that combines individual sample analysis to provide a composite analysis of the fly ash concentration and carbon concentration in a boiler exhaust duct.

It will be appreciated therefore that the apparatus and method of the present invention provide an efficient means for measuring the carbon content of a batch of fly ash in a rapid automated manner.

Whereas particular embodiments of the invention have been described above for purposes of illustration, it will be evident to those skilled in the art that numerous variations of the details may be made without departing from the invention as defined in the appended claims.

What is claimed is:

1. A method for determining carbon content in fly ash comprising, proving a source of fly ash,
   providing a microwave interrogation chamber with a choke means, a weighing means and a source of microwave power in communication therewith,
   introducing a quantity of said fly ash into said interrogation chamber through said choke means,
   arching a quantity of said fly ash by said choke means to form a self-sustaining arch of said fly ash upstream of said choke means,
   exposing said fly ash in said interrogation chamber to microwave power for a predetermined period of time,
   preventing microwaves by said choke means from entering said fly ash upstream of said choke means,
   determining the amount of carbon in said fly ash in said interrogation chamber by determining the weight of said fly ash by said weighing means and by determining the amount of said microwave energy absorbed by said fly ash through measurement of the amount of microwave energy transmitted through said fly ash and measurement of the amount of microwave energy reflected by said fly ash as related to said weight of said fly ash.

2. The method of claim 1 including,
   employing boiler exhaust gases as a source of said fly ash, and
   separating said fly ash from said exhaust gas.

3. The method of claim 1 including,
   introducing predetermined quantities of fly ash into said microwave interrogation chamber, and
   withdrawing said fly ash from said chamber after said weighing and microwave energy exposure and before introducing the next charge of fly ash into said microwave interrogation chamber.

4. The method of claim 3 including,
   providing a generally vertically oriented fly ash delivery conduit which is oriented generally perpendicular to the path of microwave power, and
   delivering said fly ash to said microwave interrogation chamber under the influence of gravity.

5. The method of claim 1 including,
   maintaining said fly ash in a stationary position with respect to said weighing means during interrogation by said microwave power.

6. The method of claim 1 including,
   after determining the weight of the carbon in said interrogated fly ash removing said fly ash from the analysis area by pneumatic means.

7. The method of claim 3 including,
   providing computer means for determining the carbon concentration of said fly ash, and
   delivering to said computer means information regarding the amount of microwave power passing through said fly ash, the amount of said microwave power reflected by said fly ash and the weight of said fly ash.

8. The method of claim 7 including,
   employing said computer means to determine the amount of said microwave power absorbed by said fly ash.

9. The method of claim 8 including,
   employing said computer means to determine the concentration of said carbon in said fly ash on a percentage weight basis.

10. The method of claim 1 including,
    providing a boiler exhaust duct as said fly ash source, and
    determining the fly ash flow rate within said duct.

11. The method of claim 1 including,
    providing said fly ash with fly ash glass and carbon content, and
    determining the amount of said fly ash glass and carbon in said fly ash.

12. The method of claim 10 including,
    said predetermined period of time being the period during which the amount of said fly ash exposed to said microwave power increases to a maximum.

13. The method of claim 11 including,
    employing a microwave waveguide having a longitudinal axis oriented generally perpendicular with respect to the opening of said choke means.

14. Apparatus for measuring carbon content of fly ash comprising,
    interrogation means for receiving said fly ash including a microwave interrogation chamber with a choke means, a weighing means and a source of microwave power in communication with said microwave interrogation chamber, fly ash supply means for supplying a quantity of said fly ash into said interrogation chamber through said choke means, said choke means including means for arching a quantity of said fly ash to form a self-sustaining arch of said fly ash upstream of said choke and means for preventing microwaves from entering said fly ash upstream of said choke means, microwave generating means for exposing said fly ash in said interrogation chamber to microwave power for a predetermined period of time, said weighing means determining the weight of said fly ash in said microwave interrogation chamber, computer means including means for receiving information regarding the weight of said fly ash in said microwave interrogation chamber and the amount of microwave energy transmitted through said fly ash and the amount of microwave energy reflected by said fly ash as related to said weight of said fly ash and means to employ said information to determine the amount of carbon in said fly ash in said interrogation chamber.

15. The apparatus of claim 14 including,
said source of microwave power is in communication with said microwave interrogation chamber by means of a microwave guide, and
said means for arching and said means for preventing microwave from entering said fly ash upstream of said choke means includes electrically conductive wires attached, in a crossing pattern, across the open end of said choke means.

16. The apparatus of claim 14 including,
pneumatic means for removing said interrogated fly ash from said apparatus.

17. The apparatus of claim 15 including,
said means for fly ash removal including pneumatic means and discharge valve means.

18. The apparatus of claim 15 including,
said interrogation chamber including an interrogation tube for receiving said fly ash.

19. The apparatus of claim 17 including,
said microwave guide having an input end and an output end.

20. The apparatus of claim 18 including,
said means for receiving the amount of microwave energy being reflected by said fly ash including dual coupler means.

21. The apparatus of claim 17 including,
said interrogation chamber being composed of a material which permits passage of microwave energy therethrough.

22. The apparatus of claim 14 including,
said computer means having means for monitoring the time interval as said interrogation chamber fills with said fly ash between when said fly ash has minimum exposure until it has maximum exposure to said microwave power.

23. The apparatus of claim 17 including,
the bottom of said interrogation chamber is provided with a plurality of openings therethrough.

* * * * *